United States Patent [19]

Rochat et al.

[11] 4,426,533

[45] Jan. 17, 1984

[54] PROCESS FOR PRODUCING BISMETHINE ISOINDOLINES

[75] Inventors: Alain C. Rochat, Basel; Luigi Cassar, Kaiseraugst, both of Switzerland

[73] Assignee: Ciba-Geigy Corporation, Ardsley, N.Y.

[21] Appl. No.: 362,580

[22] Filed: Mar. 29, 1982

[30] Foreign Application Priority Data

Apr. 6, 1981 [CH] Switzerland .......................... 2328/81

[51] Int. Cl.³ .............................................. C09B 57/04
[52] U.S. Cl. .................................... 548/471; 548/473; 548/482; 548/455; 106/288 Q; 544/284; 548/330; 548/159; 548/217
[58] Field of Search ............... 548/482, 471, 473, 455, 548/330, 159; 544/284

[56] References Cited

U.S. PATENT DOCUMENTS

| | | | |
|---|---|---|---|
| 3,390,149 | 6/1968 | Kranz et al. | 210/321 |
| 3,646,033 | 2/1972 | Leister et al. | 548/255 |
| 3,758,497 | 9/1973 | Pugin et al. | 548/460 |

FOREIGN PATENT DOCUMENTS

| | | | |
|---|---|---|---|
| 19588 | 11/1980 | European Pat. Off. | |
| 1268621 | 5/1968 | Fed. Rep. of Germany | 548/482 |
| 2041999 | 3/1972 | Fed. Rep. of Germany | |
| 2814526 | 10/1978 | Fed. Rep. of Germany | 548/482 |
| 1113530 | 5/1968 | United Kingdom | 548/471 |
| 2013230 | 8/1979 | United Kingdom | |

OTHER PUBLICATIONS

Barrett et al., "Phthalocyanines and Related Compounds . . . ", J. Chem. Soc., (1940), pp. 1076–1078.
F. Baumann et al., Angew. Chem., 68, 133, (1956).

Primary Examiner—Donald G. Daus
Assistant Examiner—G. Hendricks
Attorney, Agent, or Firm—Luther A. R. Hall

[57] ABSTRACT

A process for producing bismethine isoindolines of the formula

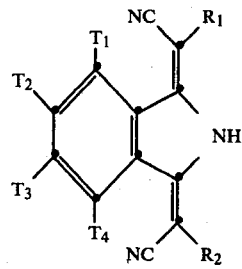

in which process the condensation of 1 mol of any one of the compounds of the formulae

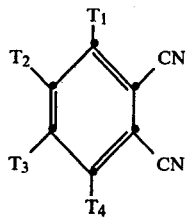 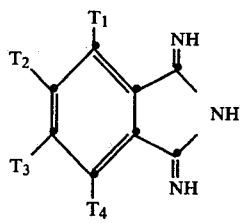

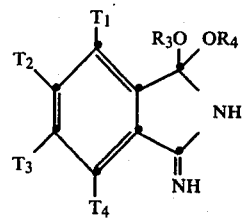

with 2 mols of a cyanomethylene compound of the formula $NC-CH_2-R_1$ or $NC-CH_2-R_2$, or with 1 mol of a cyanomethylene compound of the formula $NC-CH_2-R_1$ and 1 mol of a cyanomethylene compound of the formula $NC-CH_2-R_2$, wherein the symbols have the meanings defined in the specification, is performed in a polar solvent in the presence of a strong base, and the bismethine isoindoline obtained is isolated from the reaction mixture by hydrolysis.

The bismethine isoindolines are suitable for pigmenting high-molecular organic material, particularly lacquers.

11 Claims, No Drawings

PROCESS FOR PRODUCING BISMETHINE ISOINDOLINES

The invention relates to a process for producing bismethine isoindolines from phthalonitriles or diiminoisoindolines and active methylene compounds.

Processes using phthalonitriles as starting materials are known, in which processes the methylene components are fused-on under neutral, or preferably acidic, conditions (German Auslegeschrift No. 2,041,999). There is thus described in EP-A No. 019,588, Example 6, a process for producing a bismethine isoindoline from phthalonitrile, wherein the two methylene compounds are fused-on in the presence of an acid. The yield is 67%, and the bismethine isoindoline obtained has to be ground before it is used. Furthermore, the reaction of phthalonitrile with an active methylene component in the presence of a base is known from J. Chem. Soc., 1940, p. 1078, Examples 2 and 3. Only the monocondensation product is however obtained by this process. According to German Auslegeschrift No. 1,268,621, column 7, test report, the products obtained are moreover of inadequate purity, so that the advice given is against an alkaline process.

It was the object of the present invention to find a simplified and improved process which would yield pure and finely-crystalline bismethine isoindolines in high yield. The solution found lay in performing the condensation reaction precisely in the presence of a base.

The present invention thus relates to a simplified and improved process for producing bismethine isoindolines of the formula

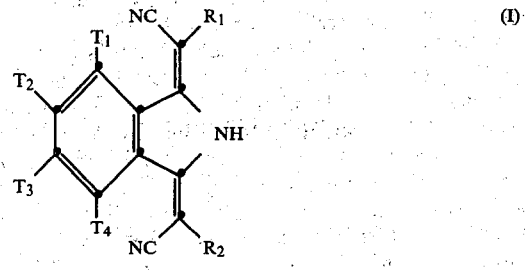

wherein $T_1$ to $T_4$ are hydrogen or halogen, or one or two of the radicals $T_1$ to $T_4$ are alkyl, alkoxy or phenoxy, and $R_1$ and $R_2$ independently of one another are each cyano, alkyl- or arylcarbonyloxy, carbamoyl, alkylcarbamoyl, or radicals of the formulae II–IV

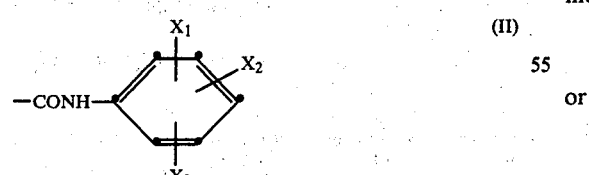

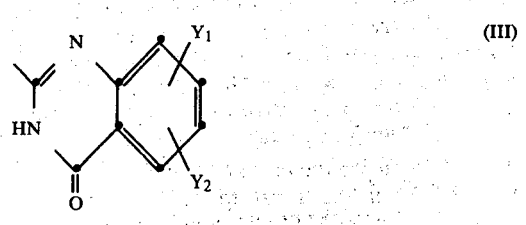

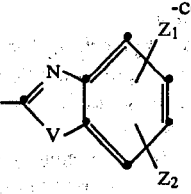

wherein $X_1$ is a non-solubilising group, and $X_2$ and $X_3$ are hydrogen, halogen, alkyl, alkoxy or alkoxycarbonyl, or together form an —NR'—CO—NR"— group, in which R' and R" independently of one another are hydrogen or $C_1$–$C_4$-alkyl, and $Y_1$ and $Y_2$ are hydrogen, halogen, alkyl or alkoxy, or together form a fused-on benzene ring, V is oxygen, sulfur, imino or alkylimino having 1 to 4 C atoms, and $Z_1$ and $Z_2$ have the meanings of $Y_1$ and $Y_2$, in which process the condensation of 1 mol of a compound of the formula V, VI or VII or of the salts of VI or VII

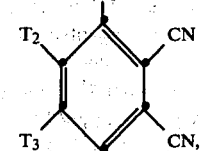

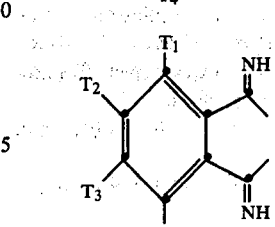

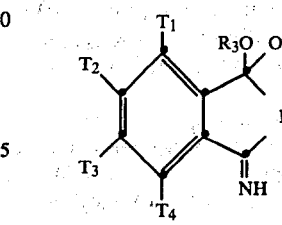

wherein $T_1$ to $T_4$ have the meanings defined above, and $R_3$ and $R_4$ are identical or different and are $C_1$–$C_4$-alkyl, or together form the group —$CH_2$—$CH_2$—, with 2 mols of a cyanomethylene compound of the formula $$NC-CH_2-R_1 \qquad (VIII)$$

or $$NC-CH_2-R_2 \qquad (IX)$$

or with 1 mol of a cyanomethylene compound of the formula VIII and 1 mol of a cyanomethylene compound of the formula IX, is performed in a polar solvent in the presence of a strong base, and the bismethine isoindoline obtained is isolated from the reaction mixture by hydrolysis.

$T_1$ to $T_4$ as halogen are in particular chlorine. When $T_1$ to $T_4$ are alkyl, it is especially that having 1 to 6 C atoms, such as ethyl, n-propyl and in particular methyl.

As alkoxy, $T_1$ to $T_4$ have especially 1 to 6 C atoms, such as ethoxy and particularly methoxy.

Alkyl in alkylcarbamoyl and alkylcarbonyloxy contains in particular 1 to 6 C atoms, such as ethyl, n-propyl, isopropyl, hexyl and especially methyl. Aryl in arylcarbonyloxy is particularly phenyl.

By a non-solubilising group $X_1$ is meant a group which does not effect a dissolving of the pigment either in water or in organic solvents. Possible groups are for example: halogen, such as fluorine, bromine or chlorine, alkyl having 1 to 6 C atoms, such as methyl, ethyl or isopropyl, also alkoxy having 1 to 6 C atoms, such as methoxy or ethoxy, also nitro, trifluoromethyl, carbamoyl, ureido, sulfamoyl or cyano, also alkoxycarbonyl, alkanoyl, alkylcarbamoyl, alkylureido, alkanoylamino, alkylsulfonyl or alkylsulfamoyl, wherein the alkyl groups each contain 1 to 6 C atoms, and are for example: methyl, ethyl, propyl, butyl or hexyl, also aryl, aryloxycarbonyl, aroyl, aroylamino, arylsulfonyl, arylcarbamoyl, arylsulfamoyl, arylureido or arylazo, wherein aryl in each case is especially phenyl and can be unsubstituted or substituted by methyl or chlorine, and also a phthalimide group which is unsubstituted or substituted in the phenyl group by chlorine.

$X_2$ and $X_3$ as halogen are in particular fluorine, bromine or chlorine. As alkyl or alkoxy, $X_2$ and $X_3$ have especially 1 to 4 C atoms, such as methyl, ethyl or butyl or methoxy, ethoxy or butoxy, and as alkoxycarbonyl they have 2 to 5 C atoms, such as in particular methoxycarbonyl or ethoxycarbonyl. In the —NR'—CO—NR"— group, which $X_2$ and $X_3$ together can form, R' and R" as $C_1$-$C_4$-alkyl are especially methyl.

$Y_1$ and $Y_2$ as halogen, alkyl or alkoxy have the same meanings as $X_2$ and $X_3$.

As alkylimino, V contains in particular 1 to 4 C atoms and is especially methylimino.

$R_3$ and $R_4$ as alkyl are particularly methyl.

Suitable salts of the compounds of the formulae VI and VII are especially those of the strong bases used in the process according to the invention, such as are described in the following.

There are preferably used as starting materials, for producing according to the invention bismethine isoindolines of the formula I, compounds of the formula V, VI or VII, especially however of the formula V, wherein $T_1$ to $T_4$ are hydrogen, and $R_3$ and $R_4$ are methyl, and cyanomethylene compounds of the formulae VIII to IX, wherein $R_1$ and $R_2$ are radicals of the formulae II to IV, wherein $X_1$ is hydrogen, fluorine, bromine, chlorine or carbamoyl, or phenylcarbamoyl unsubstituted or substituted by chlorine or methyl, $X_2$ and $X_3$ are hydrogen, fluorine, bromine or chlorine, or together form a carbodiimino group, wherein an imino group can be substituted by methyl, and $Y_1$, $Y_2$, $Z_1$ and $Z_2$ are hydrogen, bromine, chlorine, methyl or methoxy, and V is imino.

Preferred as starting materials are in particular cyanomethylene compounds of the formulae VIII to IX having radicals $R_1$ and $R_2$ of the formulae II and III, especially of the formula II, wherein $X_1$ to $X_3$ and $Y_1$ and $Y_2$ are each hydrogen or chlorine.

As starting materials are used in particular, besides a compound of the formula V wherein $T_1$ to $T_4$ are hydrogen, preferably a cyanomethylene compound of the formula X

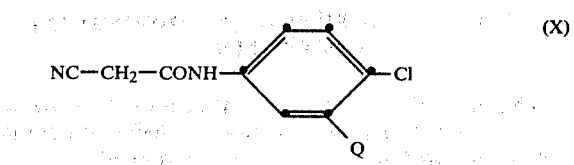

wherein Q is hydrogen or chlorine, or a cyanomethylene compound of the formula X together with one of the formula XI

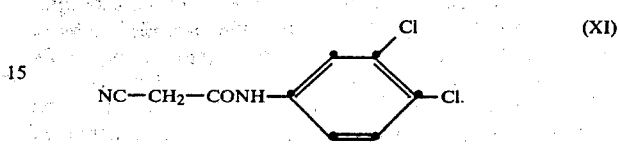

The condensation reaction is performed in a polar solvent, for example in an aliphatic alcohol having 1 to 4 C atoms, such as methanol, ethanol, isopropanol or butanol, also in a glycol, such as ethylene glycol or diethylene glycol, also in a glycol ether, such as ethylene glycol methyl ether, ethylene glycol ethyl ether, diethylene glycol monomethyl ether or diethylene glycol monoethyl ether, or in a dipolar-aprotic solvent, such as acetonitrile, benzonitrile, dimethylformamide, N,N-dimethylacetamide, nitrobenzene, dimethyl sulfoxide or N-methylpyrrolidone. Also mixtures of the stated solvents can be used. There are advantageously used 5–20 parts by weight of solvent to 1 part by weight of the reactants.

It is possible under certain conditions to use the said solvents together with water. Preferred polar solvents are aliphatic alcohols, glycols and glycol ethers. The polar solvent preferably used is methanol.

The process according to the invention is performed in the presence of a strong base, which is employed in particular in an amount of 0.9 to 1.1 mol equivalent relative to the reactants of the formula V, VI or VII. It can suffice in particular cases to use just catalytic amounts of base. Suitable strong bases are for example alkali hydroxides, such as sodium, potassium or lithium hydroxide, or alkaline-earth hydroxides, such as calcium or magnesium hydroxide, or alkali carbonates, such as sodium, potassium or lithium carbonate, or alkali alcoholates having 1 to 6 C atoms, such as sodium, potassium or lithium methylate, -ethylate, -propylate or -tert-butylate, or tert-alkylamines having a total of 3 to 18 C atoms, such as triethylamine, or alkali amides, such as lithium or sodium amide, or tetraalkylammonium hydroxides having 4 to 24 C atoms, such as tetramethylammonium hydroxide.

Preferred bases are the alkali hydroxides, alkali carbonates and alkali alcoholates.

The bases mentioned can be used together with a phase transfer catalyst. This is particularly of advantage when the solubility of a specific base in a certain solvent is low. Especially alkali carbonates in aliphatic alcohols or glycols are preferably used together with a phase transfer catalyst. The phase transfer catalysts can be employed in an amount of 0.001 to 50 mol %, preferably 0.01 to 0.3 mol %, relative to the reactants of the formula V, VI or VII. Suitable for the process according to the invention are the customary phase transfer catalysts described in the literature, such as are described for example in CHEMTECH, February, 1980, p. 111, Table 1, namely, for example quaternary salts, cyclic polyethers, open-chain polyethers, N-alkylphosphoramides, or phosphorus or sulfur oxides bridged-over with methylene. Phase transfer catalysts preferably used are quaternary salts, such as quaternary ammonium or phosphonium salts, these being in particular the halides.

Examples of quaternary ammonium or phosphonium salts are: tetrabutylammonium hydrogen sulfate, tetrabutyl-, tetrahexyl-, trioctylmethyl-, trioctylethyl-, hexyltriethyl-, octyltriethyl-, decyltriethyl-, dodecyltriethyl-, hexadecyltrimethyl-, benzyltriethyl-, tricaprylmethyl- and triphenylmethyl-ammonium- or -phosphonium-chloride, -bromide and -iodide.

The process according to the invention can be performed especially at temperatures of 0° to 180° C., preferably 50° to 110° C.

For hydrolysis of the condensation product, it is possible to use water, but preferably an acid. Suitable acids are for example: aliphatic and aromatic carboxylic or sulfonic acids, such as formic acid, acetic acid, propionic acid, oxalic acid, benzoic acid or benzenesulfonic acid. The acids used can also be mineral acids, such as hydrochloric acid, sulfuric acid or phosphoric acid.

In the hydrolysis reaction, the bismethine isoindoline precipitates, and can be isolated by filtration.

The condensation of the compound of the formula V, VI or VII with the cyanomethylene compounds is performed, preferably through all reaction stages, in the same reaction medium. Condensation in the same reaction medium means that the starting materials are reacted directly to the final material without isolation of the condensation intermediate products.

A further embodiment of the process comprises mixing, before hydrolysis, different reaction solutions which have been prepared independently of one another, and then hydrolysing them together. It is possible to isolate as salts, before hydrolysis, various condensation products, which have been prepared independently of one another, to then mix them together and to hydrolyse the mixture. A mixture of bismethine isoindolines is thus obtained.

The starting materials used in the process according to the invention are known compounds, and can be produced by processes known per se.

The process according to the invention yields the bismethine isoindolines or mixtures of bismethine isoindolines as a rule in a directly usable pigment form. These are thus obtained pigment forms which are either more transparent or more opaque.

To obtain a transparent pigment form, the hydrolysis is performed preferably at low temperatures (below 80° C.). When a more opaque pigment form is desired, it proves advantageous for hydrolysis to be carried out at a higher temperature (above 80° C.), optionally under pressure. It is also possible to add to the pigment after hydrolysis an additional solvent, and to then heat the pigment, or to firstly isolate the pigment and to subsequently heat it in water or in an organic solvent, optionally under pressure, in order to obtain the opaque form. The organic solvents preferably used are those which boil above 80° C. Particularly suitable are benzenes substituted by halogen atoms or by alkyl or nitro groups, such as xylenes, chlorobenzene, o-dichlorobenzene or nitrobenzene, as well as pyridine bases, such as pyridine, picoline or quinoline, also ketones, such as cyclohexanone, ethers, such as ethylene glycol monomethyl or monoethyl ether, amides, such as dimethylformamide or N-methylpyrrolidone, and also dimethyl sulfoxide or sulfolane. The aftertreatment can also be performed in water in the presence of organic solvents and/or with the addition of surface-active substances. Solvent aftertreatments of this kind often have a good effect on the gloss property of the pigments in lacquer dyeings.

The substances obtained by the process according to the invention are valuable pigments having high colour strength and purity of shade, and good fastness to light, weather and over-lacquering, as well as a high gloss, which pigments can be used, as a rule without additional measures, directly for pigmenting high-molecular organic materials, especially lacquers.

The following Examples illustrate the invention.

EXAMPLE 1

12.82 g of phthalonitrile and 19.45 g of cyanoacetic acid-4-chloroanilide are stirred in 200 ml of ethylene glycol monoethyl ether for 30 minutes at 20°-25° C. To the suspension are added, within 25 minutes, 18 g of a 30.8% (by weight) solution of sodium methylate in methanol; the mixture is then stirred for 1 hour at 30° C., and for 30 minutes at 40° C. The reaction mixture is cooled to 30° C., and 21.4 g of cyanoacetic acid-4-chloroanilide are added. The mixture is heated within 2 hours to 110° C., and stirred for 2½ hours at this temperature. After cooling to 60° C., the reaction solution is added, within 15 minutes, to a mixture of 8.4 g of acetic acid and 200 ml of methanol, and the suspension is refluxed for 30 minutes, and then cooled to 50° C. The pigment obtained is filtered off, and washed with 550 ml of warm methanol and with 300 ml of warm water. The yield after drying in vacuo at 70°-80° C. is 47.97 g (95.9% of theory, relative to phthalonitrile) of pure orange-red pigment of the formula XII

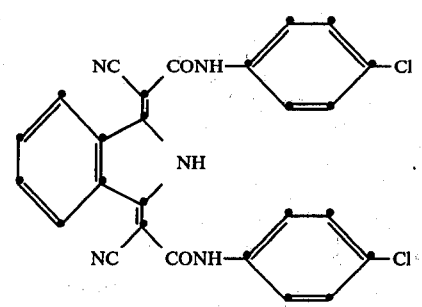

Microanalysis calculated: C 62.4%, H 3.0%, N 14.0%, O 6.4%, Cl 14.2%; found: C 62.3%, H 3.3%, N 13.9%, O 6.8%; Cl 14.0%.

The pigment has a specific surface of about 56 m²/g, and as such can be further processed in lacquers, by which means transparent and deeply coloured dyeings are obtained. By heating the pigment for one hour in o-dichlorobenzene at 100° C., there is obtained a more opaque pigment with a specific surface of about 20 m²/g, which yields very brilliant, glossy dyeings having good fastness to weather.

EXAMPLE 2

A solution of 2.1 g of lithium hydroxide monohydrate in 20 ml of methanol is added at 30° C., within 20 minutes, to 6.4 g of phthalonitrile and 21.4 g of cyanoacetic acid-4-chloroanilide in 130 ml of methanol. The reaction mixture is stirred firstly for 15½ hours at 60°–65° C., and then for 1 hour at 0° C. The reaction mixture is filtered at 0° C., and the filter cake is washed with 50 ml of ice-cold methanol. The filter cake is suspended in 130 ml of methanol, the suspension is then heated to reflux temperature, a mixture of 4.4 ml of acetic acid and 4.4 ml of methanol is added, and the mixture is refluxed for 30 minutes. After cooling to 50° C., the pigment obtained is filtered off, and washed with 450 ml of warm methanol and with 150 ml of warm water. The yield after drying in vacuo at 70°–80° C. is 23.1 g (92.4% of theory, relative to phthalonitrile) of pure orange-red pigment of the formula XII.

Microanalysis calculated: C 62.4%, H 3.0%, N 14.0%, O 6.4%, Cl 14.2%; found: C 62.3%, H 3.1%, N 14.1%, O 6.4%, Cl 13.9%.

EXAMPLE 2

A mixture of 12.8 g of phthalonitrile, 19.45 g of cyanoacetic acid-4-chloroanilide, 27.5 g of cyanoacetic acid-3,4-dichloroanilide, 13.82 g of ground potassium carbonate and 0.8 g of tricaprylmethylammonium chloride in 300 ml of ethylene glycol is heated within 6 hours to 100° C. The suspension is stirred for 1 hour at 100° C.; it is then cooled to 70° C., and slowly added, within 10 minutes, to a mixture, at 40° C., of 8.4 ml of acetic acid and 200 ml of methanol. The whole is refluxed for 30 minutes; the pigment obtained is filtered off, and washed with 600 ml of warm methanol and with 250 ml of warm water. The yield after drying is 52.1 g (97.5% of theory, relative to phthalonitrile) of an orange mixture which is usable directly as pigment, and which consists principally of the pigment of the formula XIII

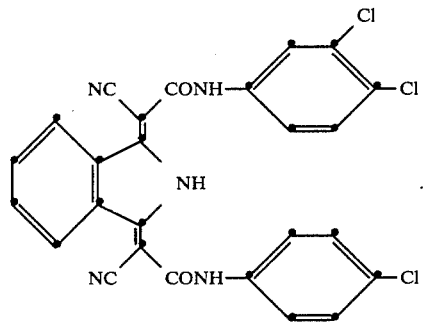

Microanalysis calculated: C 58.4%, H 2.6%, N 13.1%, O 6.0%, Cl 19.9%; found: C 57.8%; H 2.9%, N 12.8%, O 6.1%, Cl 20.4%.

EXAMPLE 4

1.32 g of a 30.8% (by weight) solution of sodium methylate in methanol are added to 0.98 g of phthalonitrile in 15 ml of methanol, whereupon 1,1-dimethoxy-3-iminoisoindoline is formed as the sodium salt with high yield (cp. Angew. Chem., 68, 134–135 and 138–140 (1956)). After 30 minutes' stirring at 20°–25° C., there are added 3.63 g of 5-cyanoacetamino-1-methyl-benzimidazol-2-one. The suspension is firstly stirred at 30° C. for 90 minutes, and then refluxed for 90 minutes. 20 ml of ethylene glycol monoethyl ether are added, and the mixture is heated to 85° C., in the course of which the methanol is distilled off. Stirring is maintained for a further 30 minutes at 85° C., and the temperature is then lowered to 40° C. To the suspension are added 25 ml of methanol and 3.9 ml of acetic acid, and the mixture is refluxed for 30 minutes. It is cooled to 50° C. and the pigment obtained is filtered off; it is subsequently washed with 200 ml of warm methanol and with 100 ml of warm water. The yield after drying is 3.41 g (79.7% of theory, relative to phthalonitrile) of pure brown pigment of the formula XIV

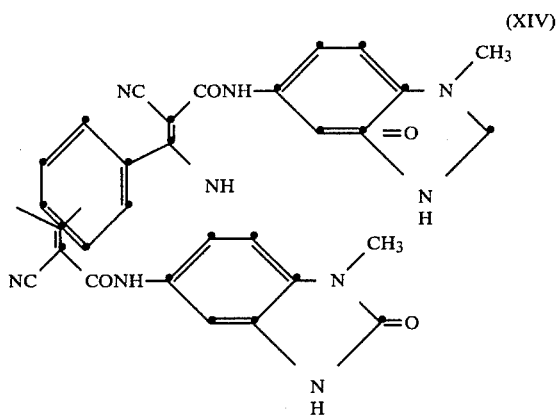

Microanalysis calculated: C 61.1%; H 3.9%, N 21.4%, O 13.6%; found: C 60.6%, H 4.0%, N 21.9%, O 13.2%.

EXAMPLE 5

7.86 g of 82% benzimidazol-2-yl-acetonitrile are dissolved in 30 ml of anhydrous dimethyl sulfoxide at 20°–25° C., and 5.61 g of potassium tert-butylate are then added within 7 minutes. Stirring is maintained for 12 minutes at 20°–25° C., and 6.4 g of phthalonitrile are added. The reaction solution is heated in stages to 80° C., and is stirred for 70 minutes at this temperature. After cooling of the reaction solution to 50° C., 7.86 g of 82% benzimidazol-2-yl-acetonitrile are added; the temperature is raised to 120° C., and stirring is continued at this temperature for 155 minutes. The reaction solution is subsequently cooled to 75° C.; 6 ml of acetic acid and 120 ml of methanol are added, and the whole is refluxed for 30 minutes. After cooling to 40° C., the pigment obtained is filtered off, and is washed with 100 ml of methanol and with a mixture of 50 ml of methanol and 50 ml of water, and finally with 50 ml of water. The yield after drying in vacuo at 70° C. is 15.95 g (91.5% of theory, relative to 100% benzimidazol-2-yl-acetonitrile) of pure bluish-red pigment of the formula XV

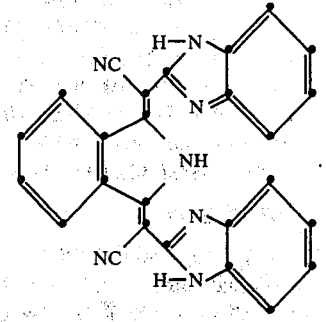

(XV)

Microanalysis calculated: C 73.4%, H 3.6%, N 23.1%; found: C 72.7%, H 3.5%, N 22.6%.

EXAMPLE 6

To 3.2 g of phthalonitrile and 10.2 g of 2-cyanomethylquinazolone in 60 ml of ethylene glycol are added 4.38 g of a 30.8% (by weight) solution of sodium methylate in methanol, and the suspension is stirred for 30 minutes at 20°–25° C. It is then heated to 60° C. and stirred for 2 hours at this temperature; it is heated further to 90° C. and held at that temperature for 2 hours, and is stirred finally for 3 hours at 110° C. After cooling to 80° C., the suspension is added to a mixture, at 40° C., of 1.9 ml of acetic acid and 100 ml of ethylene glycol monoethyl ether. The mixture is stirred for 30 minutes at 40° C., and for 1 hour at 65° C. The pigment obtained is filtered off warm, and subsequently washed with 250 ml of ethylene glycol monoethyl ether, 400 ml of methanol and 100 ml of water. The yield after drying is 9.4 g (78.1% of theory, relative to phthalonitrile) of pure orange-brown pigment of the formula XVI

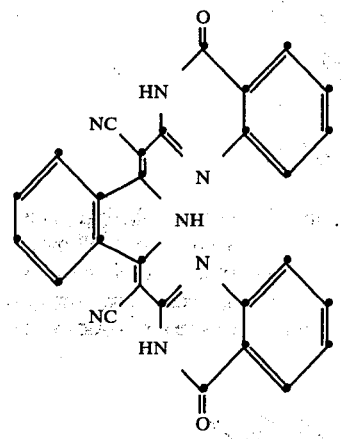

(XVI)

Microanalysis calculated: C 69.9%, H 3.1%, N 20.4%, O 6.6%; found: C 68.3%, H 3.5%, N 21.0%, O 7.1%.

EXAMPLE 7

17.54 g of a 30.8% (by weight) solution of sodium methylate in methanol are added to 12.8 g of phthalonitrile in 200 ml of ethylene glycol. After 30 minutes' stirring at 20°–25° C., 27.5 g of cyanoacetic acid-3,4-dichloroanilide are added, and the mixture is stirred at 28°–30° C. for 2½ hours. There are subsequently added 19.45 g of cyanoacetic acid-4-chloroanilide, and the mixture is heated within 30 minutes to 65° C. After 2 hours at 65° C., the suspension is heated within 30 minutes to 100° C., and is held at this temperature for 2 hours. The suspension is cooled to 60° C., and is added, within about 5 minutes, to a mixture, at 40° C., of 7.2 ml of acetic acid and 300 ml of methanol. The mixture is stirred for 30 minutes, and then refluxed for 30 minutes; it is afterwards cooled to about 50° C., and the pigment is filtered off. It is washed with 400 ml of warm methanol and with 300 ml of warm water. The yield after drying is 52.9 g (99.0% of theory, relative to phthalonitrile) of an orange mixture consisting principally of the pigment of the formula XIII. The pigment has a specific surface of about 53 m²/g, and as such can be further processed in lacquers, with which transparent dyeings having high colour strength are obtained.

Microanalysis calculated: C 58.4%, H 2.6%, N 13.1%, Cl 19.9%; found: C 57.6%, H 2.5%, N 13.0%, Cl 20.1%.

These is obtained by heating for two hours at 130° C. in o-dichlorobenzene a considerably more opaque pigment having a specific surface of about 20 m²/g.

EXAMPLE 8

A mixture of 6.4 g of phthalonitrile, 10.1 g of cyanacetamide, 2.0 g of caustic soda and 100 ml of absolute ethanol is refluxed for 19 hours (about 76° C.). The suspension is then allowed to cool to 50° C.; 6 ml of acetic acid are then added, and the mixture is briefly refluxed again. The pigment is subsequently filtered off, washed with 150 ml of warm ethanol and with 100 ml of warm water, and dried at 80° C. in vacuo. The yield is 13.6 g (97.5% of theory, relative to phthalonitrile) of pure greenish-yellow pigment of the formula XVII.

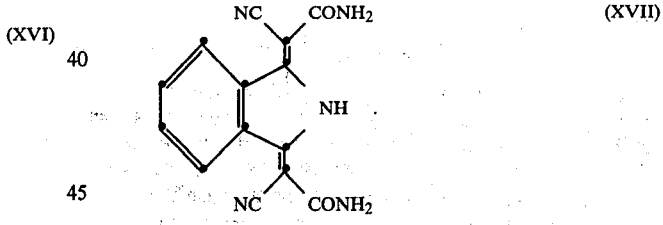

(XVII)

Microanalysis calculated: C 60.22%, H 3.25%, N 25.08%; found: C 60.0%, H 3.50%, N 24.70%.

EXAMPLE 9

A mixture of 6.4 g of phthalonitrile, 21.4 g of cyanoacetic acid-4-chloroanilide, 7.6 g of ground potassium carbonate and 1.4 g of polyoxyethylene lauryl ether (Brij 35 ®) in 130 ml of methanol is heated within 30 minutes to reflux temperature (about 65° C.), and refluxed for 10 hours. The resulting pigment suspension is cooled to 50° C., and then added, within 10 minutes, to a mixture, at 40° C., of 7.3 ml of acetic acid and 125 ml of methanol. The mixture is refluxed for 30 minutes, and again cooled to about 50° C. The pigment is filtered off, washed with 350 ml of warm methanol, then with 200 ml of warm water, and dried at 100° C. in vacuo. The yield is 24.38 g of pure orange-red pigment of the formula XII (97.5% of theory, relative to phthalonitrile). The product results in transparent lacquer dyeings.

Microanalysis calculated: C 62.4%, H 3.0%, N 14.0%, O 6.4%, Cl 14.2%; found: C 62.0%, H 3.2%, N 13.8%, O 6.7%, Cl 14.0%.

When the pigment suspension, after addition thereof to acetic acid and methanol, is heated for 2 hours at 95° C. under slight pressure (1.7 bar), and subsequently processed as described above, there are obtained 23.5 g of pure orange-red pigment of the formula XII, corresponding to a yield of 94% of theory, relative to phthalonitrile. The product gives opaque lacquer dyeings. Both forms of pigment (transparent and opaque) are directly usable as such in lacquer manufacture.

EXAMPLE 10

A mixture of 6.4 g of phthalonitrile, 9.73 g of cyanoacetic acid-4-chloroanilide, 13.75 g of cyanoacetic acid-3,4-dichloroanilide, 7.6 g of ground potassium carbonate and 1.5 g of polyoxyethylene lauryl ether (Brij 35 ®) in 160 ml of methanol is heated within 30 minutes to reflux temperature, and is refluxed for 12 hours. The pigment suspension obtained is cooled to 50° C., and is added within 10 minutes to a mixture, at 40° C., of 7.3 ml of acetic acid and 125 ml of methanol. The mixture is refluxed for 30 minutes and again cooled to about 50° C. The pigment is filtered off, washed with 400 ml of warm methanol, then with 150 ml of warm water, and dried at 50° C. in vacuo. The yield is 26.7 g (99.9% of theory, relative to phthalonitrile) of an orange mixture consisting mainly of the pigment of the formula XIII. The mixture is directly usable for lacquer manufacture, and produces very transparent dyeings having high colour strength.

Macroanalysis calculated: C 58.4%, H 2.6%, N 13.1%, O 6.0%, Cl 19.9%; found: C 57.7%, H 2.8%, N 13.0%, O 6.3%, Cl 20.1%.

EXAMPLE 11

12.82 g of phthalonitrile, 39.16 g of cyanoacetic acid-3-fluroranilide and 15.18 g of potassium carbonate in 500 ml of methanol are heated to reflux temperature. After 10 hours at this temperature, 20 ml of acetic acid are added, and the reddish-yellow pigment is filtered off hot. It is washed with methanol and water, and the yield after drying is 42.3 g of pigment of the formula XVIII

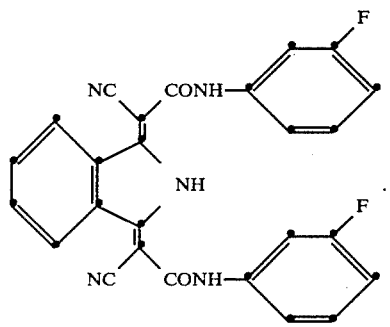

(XVIII)

Microanalysis calculated: C 66.81%, H 3.23%, N 14.98%, F 8.13%; found: C 66.6%, H 3.3%, N 15.20%, F 7.9%.

The pigment can be used as such in lacquers, whereby reddish-yellow dyeings having high colour strength are obtained. By heating for one hour in o-dichlorobenzene, there is obtained a particularyl opaque pigment form. The pigment is advantageously converted, by grinding or kneading, into a finely-divided form. After incorporation thereof into lacquers, there are obtained opaque dyeings having a high colour strength, high gloss and good fastness properties, in particular excellent fastness to light and to weather.

EXAMPLE 12

A mixture of 9.68 g of 75% (by weight) Phthalogen-brillantblau IF 3G ® (a 1,3-diiminoisoindoline, Bayer), 21.4 g of cyanoacetic acid-4-chloroanilide, 7.6 g of ground potassium carbonate and 1.4 g of polyoxyethylene lauryl ether (Brij 35 ®, Atlas Powder) in 180 ml of methanol is heated within 30 minutes to reflux temperature, and is held for 18 hours at this temperature. The suspension is cooled to 50° C., and a mixture of 9.2 ml of glacial acetic acid and 25 ml of methanol is added within 10 minutes. The mixture is refluxed for 30 minutes, cooled to 50° C. and filtered. The filter residue is washed with 200 ml of warm methanol and with 100 ml of warm water. The yield after drying at 80° C. in vacuo is 23.75 g (95% of theory, relative to 1,3-diiminoisoindoline) of pure orange-red pigment of the formula XII.

Microanalysis calculated: C 62.4%, H 3.02%, N 14.0%, Cl 14.17%; found: C 62.2%, H 3.2%, N 14.0%, Cl 14.0%.

What is claimed is:

1. A process for producing bismethine isoindolines of the formula

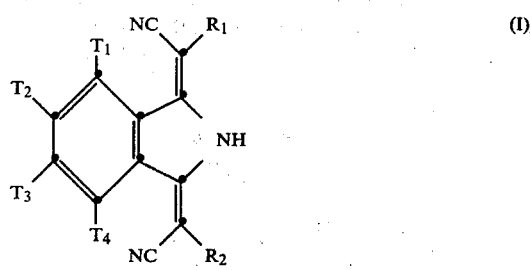

(I)

wherein $T_1$ to $T_4$ are hydrogen or halogen, or one or two of the radicals $T_1$ to $T_4$ are alkyl, alkoxy or phenoxy, and $R_1$ and $R_2$ independently of one another are each cyano, alkyl- or arylcarbonyloxy, carbamoyl, alkylcarbamoyl, or radicals of the formulae II to IV

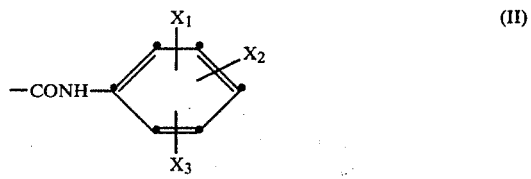

(II)

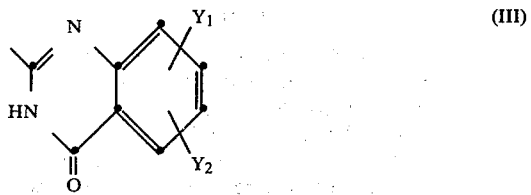

(III)

-continued

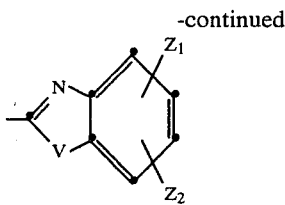
(IV)

wherein $X_1$ is a non-solubilising group, and $X_2$ and $X_3$ are hydrogen, halogen, alkyl, alkoxy or alkoxycarbonyl, or together form an —NR'—CO—NR"— group, in which R' and R" independently of one another are hydrogen or $C_1$-$C_4$-alkyl, and $Y_1$ and $Y_2$ are hydrogen, halogen, alkyl or alkoxy, or together form a fused-on benzene ring, V is oxygen, sulfur, imino or alkylimino having 1 to 4 C atoms, and $Z_1$ and $Z_2$ have the meanings of $Y_1$ and $Y_2$, in which process the condensation of 1 mol of a compound of the formula V, VI or VII or of the salts of VI or VII

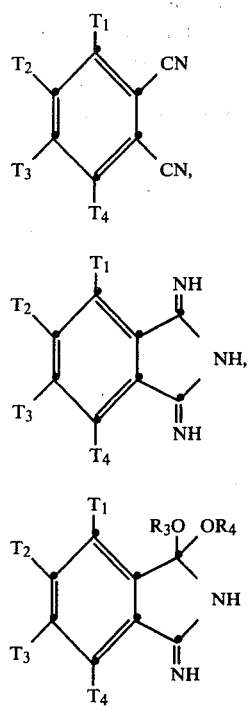

(V)

(VI)

(VII)

wherein $T_1$ to $T_4$ have the meanings defined above, and $R_3$ and $R_4$ are identical or different and are $C_1$-$C_4$-alkyl, or together form the group —$CH_2$—$CH_2$—, with 2 mols of a cyanomethylene compound of the formula

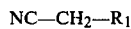
NC—$CH_2$—$R_1$ (VIII)

or

NC—$CH_2$—$R_2$ (IX), or with 1 mol of a cyanomethylene compound of the formula VIII and 1 mol of a cyanomethylene compound of the formula IX, wherein $R_1$ and $R_2$ have the meanings defined above, is performed in a polar solvent in the presence of a strong base, and the bismethine isoindoline obtained is isolated from the reaction mixture by hydrolysis in the presence of an acid.

2. A process according to claim 1, wherein the starting material used is a compound of the formula V, VI or VII in which $T_1$ to $T_4$ are hydrogen, and $R_3$ and $R_4$ are methyl.

3. A process according to claim 1, wherein the starting material used is a compound of the formula V in which $T_1$ to $T_4$ are hydrogen.

4. A process according to claim 1, wherein the starting materials used are cyanomethylene compounds of the formulae VIII to IX having the radicals $R_1$ and $R_2$ of the formulae II to IV in which $X_1$ is hydrogen, bromine, chlorine or carbamoyl, or phenylcarbamoyl unsubstituted or substituted by chlorine or methyl, $X_2$ and $X_3$ are hydrogen, fluorine, bromine or chlorine, or together form a carbodiimino group, wherein an imino group can be substituted by methyl, and $Y_1$, $Y_2$, $Z_1$ and $Z_2$ are hydrogen, bromine, chlorine, methyl or methoxy, and V is imino.

5. A process according to claim 1, wherein the starting materials used are cyanomethylene compounds of the formulae VIII to IX having the radicals $R_1$ and $R_2$ of the formula II in which $X_1$ to $X_3$ are hydrogen or chlorine.

6. A process according to claim 1, wherein the starting materials used are unsubstituted phthalonitrile and cyanomethylene compounds of the formulae

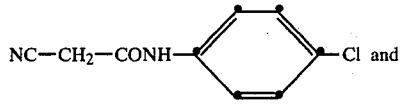
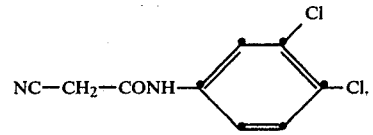
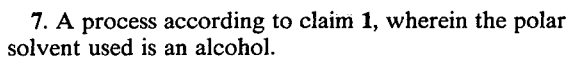

7. A process according to claim 1, wherein the polar solvent used is an alcohol.

8. A process according to claim 1, wherein the strong base used is an alkali hydroxide, alkali carbonate or alkali alcoholate.

9. A process according to claim 1, wherein the base is used together with a phase-transfer catalyst.

10. A process according to claim 1, wherein the condensation is performed, through all reaction stages, in the same reaction medium.

11. A process according to claim 1, wherein an organic acid is used for the hydrolysis reaction.

* * * * *